United States Patent [19]

Nagel

[11] 4,336,368

[45] Jun. 22, 1982

[54] 4 DEOXY-4-METHYLENE OLEANDOMYCIN AND DERIVATIVES THEREOF

[75] Inventor: Arthur A. Nagel, Gales Ferry, Conn.

[73] Assignee: Pfizer Inc., New York, N.Y.

[21] Appl. No.: 255,620

[22] Filed: Apr. 20, 1981

[51] Int. Cl.$^3$ .................. C07H 17/08; A01N 9/00
[52] U.S. Cl. ............................ 536/7.2; 424/180; 536/7.3; 536/7.4
[58] Field of Search ............... 536/9, 17 R; 424/180, 424/181

[56] References Cited

U.S. PATENT DOCUMENTS

| | | | |
|---|---|---|---|
| 4,085,119 | 4/1978 | Myers | 260/343 |
| 4,090,017 | 5/1978 | Sciavolino | 536/9 |
| 4,124,755 | 11/1978 | Bright | 536/9 |

Primary Examiner—Blondel Hazel
Attorney, Agent, or Firm—Charles J. Knuth; Albert E. Frost; Peter C. Richardson

[57] ABSTRACT

Derivatives of oleandomycin, its 11-trimethylsilyl ether and 11-trimethylsilyl-2'-alkanoyl esters and processes for preparation thereof wherein the L-oleandrosyl moiety is modified at the 4"-position to provide derivatives thereof wherein said moiety has formula (a) or (b)

wherein
A and B when taken together are =CHX wherein X is H, —CN, —COOR$_3$, —SR$_3'$, —S(O)R$_3'$, —S(O)$_2$R$_3'$ or —N=CH—(aryl-R$_4$);

A when taken individually is hydrogen;
B when taken individually is —CHO or —CH$_2$Z wherein Z is hydrogen, —OR$_3$, —COOR$_3$, —SR$_3'$, —S(O)R$_3'$, —S(O)$_2$R$_3'$, —CN or —(CH$_2$)$_n$—NR$_5$R$_6$;

R$_3$ is hydrogen, (C$_{1-4}$)alkyl or —(aryl-R$_4$);

R$_3'$ is (C$_{1-4}$)alkyl or

—(aryl-R$_4$);

R$_4$ is hydrogen, chloro, bromo, (C$_{1-4}$)alkyl or (C$_{1-4}$)alkoxy;
R$_5$ is hydrogen or —CH$_2$—(aryl-R$_4$);

R$_6$ is hydrogen, —COCH$_3$,

—CH$_2$—(aryl-R$_4$), —SO$_2$—(aryl-R$_4$),

—CO—(isoxazolyl) or —CO—(pyridyl);

R$_5$ and R$_6$ when taken together with the nitrogen to which they are attached are phthalimido;
n is 0 or 1;
or a pharmaceutically acceptable acid addition salt thereof of a compound wherein B is —CHO or —CH$_2$Z.

The compounds are antibacterial agents. Additionally, those compounds wherein the oleandrosyl moiety is of formula (b), or of formula (a) wherein A is hydrogen and B is CHO, and those wherein A and B when taken together are =CH—X, are useful as intermediates for formula (a) derivatives wherein A is hydrogen and B is —CH$_2$Z.

19 Claims, No Drawings

4 DEOXY-4-METHYLENE OLEANDOMYCIN AND DERIVATIVES THEREOF

BACKGROUND OF THE INVENTION

1. Field of the Invention

This invention relates to a structurally unique group of semisynthetic macrolides and, more particularly, to derivatives of oleandomycin, its 11-trimethylsilyl ether and 11-trimethylsilyl-2'-alkanoyl esters having at the 4"-position a methylene (=CH$_2$) group and to various products derived therefrom via Wittig type reactions.

2. Description of the Prior Art

Oleandomycin, its production in fermentation broths and its use as an antibacterial agent was first described in U.S. Pat. No. 2,757,123. The naturally occurring compound is known to have the following structure:

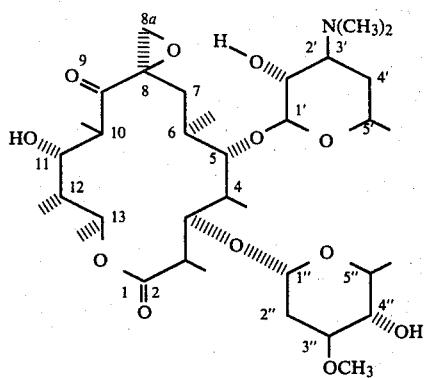

The conventionally accepted number scheme and stereochemical representation for oleandomycin and similar compounds is shown at a variety of positions. It consists of three main structural features: the L-oleandrose moiety, the desosamine moiety and the oleandolide moiety.

Derivatization of oleandomycin has focused primarily upon the formation of esters at one or more of three hydroxy groups located at the 2',4" and 11-positions. Mono-, di- and triacyl esters wherein the acyl moiety is derived from a lower aliphatic hydrocarbon monocarboxylic acid having from two to six carbon atoms are described in U.S. Pat. No. 3,002,219.

More recently, oleandomycin derivatives modified at the 4"-position have been described. For example, U.S. Pat. No. 4,125,705 describes 4"-deoxy-4"-oxo, oximido and amino derivatives; U.S. Pat. No. 4,085,119 discloses 4"-deoxy-4"-substituted amino derivatives wherein the substitutent is —(CH$_2$)$_n$Z—R wherein n is an integer of 1-4 and Z is O, S, SO, SO$_2$, NH, CO or CHOH and R is phenyl, substituted phenyl or heterocyclyl; U.S. Pat. No. 4,090,017 describes 4"-substituted amino derivatives wherein the substituent is a phenyl, benzyl or heterocyclylmethyl group. Still further, U.S. Pat. No. 4,124,755 reports on 4"-deoxy-4"-isonitrilo and 4-deoxy-4"-formamido-oleandomycins.

SUMMARY OF THE INVENTION

There has now been found a structurally unique group of oleandomycin derivatives each member of which exhibits valuable antibacterial activity in vivo, and many of which exhibit in vivo antibacterial activity via the parenteral and oral routes of administration, particularly against Gram-positive microorganisms. The compounds of this invention have formula I

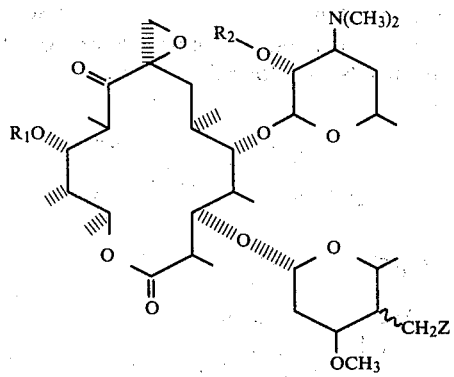

wherein
R$_1$ is hydrogen or trimethylsilyl;
R$_2$ is hydrogen or alkanoyl having from two to three carbon atoms;
Z is H, —OR$_3$, —COOR$_3$, —SR$_3'$, —S(O)R$_3'$, —S(O)$_2$R$_3'$, —CN or —(CH$_2$)$_n$—NR$_5$R$_6$;
R$_3$ is hydrogen, alkyl having from one to four carbon atoms or

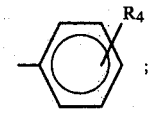

R$_3'$ is alkyl having from one to four carbon atoms or

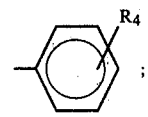

R$_4$ is hydrogen, chloro, bromo, alkyl having from one to four carbon atoms or alkoxy having fron one to four carbon atoms;
R$_5$ is hydrogen or

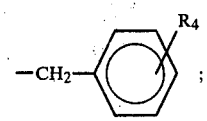

R$_6$ is hydrogen,

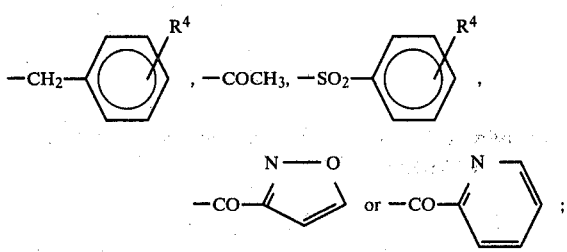

R$_5$ and R$_6$ when taken together with the nitrogen to which they are attached are phthalimido;
and n is 0 or 1;

or a pharmaceutically acceptable acid addition salt thereof.

Also included in this invention are the following compounds useful as antibacterial agents and as intermediates for preparation of compounds of formula I. These compounds have formulae II-IV below:

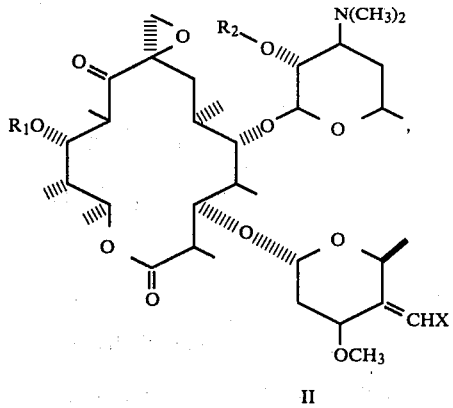

II

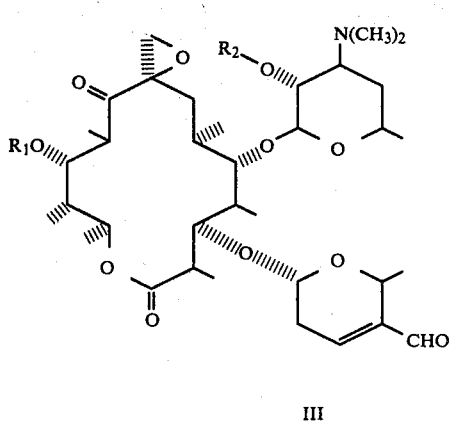

III and

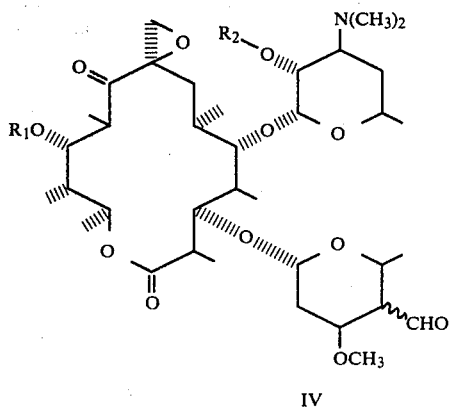

IV wherein each of $R_1$ and $R_2$ is as previously defined; and X is hydrogen, —CN,

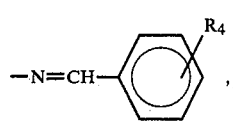

—$COOR_3$, —$SR_3'$, —$S(O)R_3'$, or —$S(O)_2R_3'$; and each of $R_3$, $R_3'$ and $R_4$ is as previously defined;

or a pharmaceutically acceptable acid addition salt thereof.

Representative of pharamceutically acceptable acid addition salts, but not limited thereto, are salts formed with inorganic or organic acids such as hydrochloric, hydrobromic, phosphoric, sulfuric, formic, acetic, propionic, butyric, citric, glycolic, lactic, tartaric, malic, maleic, gluconic, fumaric, stearic, mandelic, pamoic, benzoic, p-toluenesulfonic, sulfosalicylic, succinic and aspartic acids.

In formulae I and IV above, the wavy line connecting the group at the 4″-position of the oleandrosyl moiety is generic to and embracive of both the axial and equatorial epimeric forms.

Broken line attachment of the 4″-position substituent $CH_2Z$ or CHO represents, arbitrarily, the equatorial configuration, and solid line attachment represents, arbitrarily, the axial configuration.

The herein described compounds, especially those of formula I, including the epimeric forms thereof, and their pharmaceutically acceptable salts are effective antibacterial agents against Gram-positive microorganisms, e.g. *Staphylococcus aureus* and *Streptococcus pyogenes*, in vitro and many are active in vivo via the parenteral and oral routes of administration. Many of the compounds (and their salts) are also active against certain Gram-negative microorganisms, such as cocci, e.g. *Pasteurella multocida* and *Neisseria sicca*.

Favored because of their greater antibacterial activity and potency are those compounds of formula I wherein $R_2$ is hydrogen or acetyl; $R_1$ is hydrogen and Z is —$(CH_2)_n$—$NR_5R_6$, —$S(O)_2R_3'$.

Preferred compounds are those wherein each of $R_1$ and $R_2$ is hydrogen and Z is —$CH_2$-phthalimido, —NH-benzyl and —$SO_2CH_3$.

DETAILED DESCRIPTION OF THE INVENTION

The compounds of this invention are prepared via stabilized anion chemistry (e.g., Wittig-type reaction) with an appropriate 4″-deoxy-4″-oxooleandomycin reactant; the reaction being, in effect, replacement of the 4″-carbonyl oxygen (oxo) by a =CHX group wherein X is as defined above. Said compounds (formula II) are antibacterial agents and intermediates for further synthesis.

The Wittig reaction and variants thereof described herein comprise reaction of a carbonyl containing compound under mild conditions with a phosphate ester $(R^oO)_2P(O)CH_2X$ in a reaction-inert solvent in the presence of a base ($R^o=C_{1-4}$ alkyl and X is as defined above).

The general procedure comprises reacting the carbonyl compound 4″-deoxy-4″-oxooleandomycin, the 11- and 2′-hydroxy groups of which are protected by groups easily removable from the final product, in the presence of a base with an appropriate dialkyl phosphonate, e.g. $(C_2H_5O)_2P(O)CH_2X$ wherein X is as defined above, in a reaction-inert solvent.

As will be recognized by those skilled in the art, a variety of protecting groups can be used. The principle criteria for such groups are that they be readily available, they react easily with the 11- and/or 2′-hydroxy groups to replace the hydrogen thereof in good yield, they be stable under the reaction conditions to which said protected compounds are subjected, and they be removable under relatively mild conditions.

The function of the protecting groups is to protect said 11- and 2'-hydroxy groups during reactions leading to formula II and I products. It is the ability of said protecting groups to perform the specific function of protecting said hydroxy groups rather than their structures which are important. The selection and identification of appropriate protecting groups can easily and readily be made by one skilled in the art. The suitability and effectiveness of a group is determined by employing such a group in the reactions described herein and its subsequent ease of removal to permit restoration of the 11- and 2'-hydroxy groups.

The different reactivities of the 11- and 2'-hydroxy groups allow the use of the same or different protecting groups. However, from a practical standpoint, e.g. ease of preparation and subsequent restoration of the hydroxy groups, it is preferred to protect the 2'-hydroxy group by esterification as the 2'-acetyl or 2'-propionyl derivative, and the 11-hydroxy group as a trialkylsilyl ether, especially as the trimethylsilyl ether. The 2'-acetyl or 2'-propionyl derivatives are prepared by known procedures (U.S. Pat. No. 4,125,705). The 11-trimethylsilyl and other trialkylsilyl ethers are also prepared by known procedures, for example, by reacting 2'-acetyl-4"-deoxy-4"-oxooleandomycin with an appropriate silylating agent, e.g., trimethylsilyl chloride, in a reaction-inert solvent and in the presence of an acid acceptor.

The 11-trimethylsilyl protecting group is easily removed by acid hydrolysis or by reaction with tetra-n-butylammonium fluoride and the 2'-acetyl (or propionyl) group by solvolysis according to known procedures.

The synthesis of formula II compounds is accomplished by reacting 2'-acetyl-4"-deoxy-4"-oxooleandomycin 11-trimethylsilyl (TMS) ether with the appropriate phosphonate ester $(R^oO)_2P(o)CH_2X$ in the presence of a base and in a reaction-inert solvent.

A variety of bases can be used typical of which are organometallics such as phenyl lithium or n-butyl lithium, and alkali metal alkoxides such as sodium, potassium and lithium alkoxides of $C_{1-4}$ alcohols.

When using an organometallic base suitable solvents are aliphatic and cyclic ethers such as diethyl ether, dioxane, tetrahydrofuran and bis(2-methoxyethyl)ether. Suitable solvents when an alkali metal alkoxide is used as base are alcohols corresponding to the alkoxide moiety.

Still further bases which can be used are alkali metal hydrides, e.g. NaH, in dimethylsulfoxide as solvent.

The reaction is carried out, in general, by reacting equimolar amounts of the 2'-acetyl-4"-deoxy-4"-oxooleandomycin 11-TMS ether, phosphonate and base in an appropriate solvent at temperatures ranging from about $-70°$ to about $-20°$ C. when using an organometallic base and at from about $-10°$ C. to $20°$ C. when using an alkoxide as base. The reactions are allowed to continue until complete, usually from about 1-4 hours.

The products are isolated by standard procedures such as by partition of the reaction residue between a buffered, basic aqueous phase and an organic phase in which the product is soluble. Final purification can be achieved by column or high pressure liquid chromatographic techniques or by crystallization.

The products of the stabilized ion chemistry, formula II compounds, are by reason of their unsaturation at the point of attachment of group =CHX at the 4"-position, and because of the functionality in substituent X (wherein X is as previously defined), also valuable intermediates for further synthesis of compounds of formulae I, III and IV, all of which are antibacterial agents.

For example, the methylene or substituted methylene group at the 4"-position can be reduced to a methyl or substituted methyl group ($-CH_2Z$ wherein Z is as defined above). Catalytic hydrogenation over a noble metal catalyst, supported or unsupported, at pressures ranging from about 0.07 to about 7 kg./cm.$^{-2}$ (1-100 psi) at temperatures from about $20°$ C. to $50°$ C. in a reaction-inert solvent afford a convenient method for converting =CHX to $-CH_2Z$. Higher pressures and temperatures can, of course, be used but offer no advantages. Their use suffers from the disadvantage of requiring pressure apparatus. Suitable noble metal catalysts are platinum, palladium or rhodium. It is preferred to use a supported catalyst, e.g. Pd/C, since better distribution of the metal in the reaction mixture is achieved.

When substituent X is a cyano (CN) group, it is readily converted to aminomethyl by catalytic hydrogenation over a metal, preferably a noble metal catalyst, such as those described above, and particularly over rhodium on alumina. The reaction conditions are the same as those previously described for reduction of =CHX groups. The presence of ammonia during the reduction is desirable to minimize formation of by-products. In this regard molar proportions of ammonia ranging from about 0.05 to about 1.0 mole per mole of cyano reactant are satisfactory.

The amino group can then be subjected to various reactions such as alkylation and acylation to provide N-substituted derivatives.

A highly versatile intermediate is produced by using a diethyl benzylideneaminomethyl phosphonate as reactant in the Wittig reaction. The compound of formula II produced wherein X is

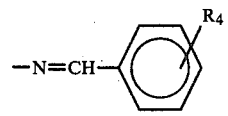

is a Schiff base and serves as intermediate for compounds of formulae III and IV above. Reaction with acid, i.e., acid hydrolysis, at pH of from about 1.0 to 4.0 affords compound III, a 3-des(oleandrosyloxy)-3-(3",4"-dehydro-4"-formyl-5"-methylpyran-1"-yloxy)oleandomycin.

Reduction of said compound III, the 11- and 2'-hydroxy groups of which are protected as described above, with a metal hydride such as sodium borohydride, lithium aluminum hydride or potassium tri-sec-butylborohydride, affords the corresponding 3-des-(oleandrosyloxy)-3-(3",4"-dehydro-4"-hydroxymethyl-5"-methylpyran-1"-yloxy)oleandomycin compound. Hydrogenation of said compound over Pd/C as described above produces the corresponding 4"-deoxy-4"-hydroxymethyl oleandomycin derivative (I, Z=OH).

Catalytic hydrogenation of the unsaturated formyl derivative III according to procedures described above, and preferably over Pd/C as catalyst, affords the saturated formyl derivative IV. Said compound is also produced by hydrolysis of the above mentioned Schiff base

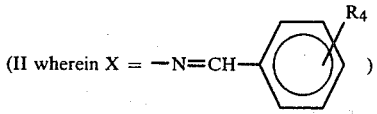
(II wherein X = —N=CH—⟨phenyl-R4⟩)

at pH about 6.0.

Other compounds of formula II wherein X is —COOR$_3'$, SR$_3'$, S(O)R$_3'$ and S(O)$_2$R$_3'$ are produced by employing the appropriate dialkyl phosphonate, e.g., (C$_2$H$_5$O)$_2$P(O)CH$_2$R$_3'$ according to procedures described above.

Compounds of formulae I and IV can, as noted above, exist in epimeric forms or as mixtures thereof. Said epimeric forms can be separated by chromatography on silica gel using appropriate solvents such as chloroform-methanol, chloroform-isopropyl ether, acetone or ethyl acetate.

A convenient method for producing a compound of formula II wherein =CHX is =CH$_2$, comprises reaction of 2'-acetyl-4"-deoxy-4"-oxooleandomycin 11-TMS ether with N,S-dimethylamino-S-phenylsulfoximine and n-butyl lithium at a temperature of $-50°$ to $-70°$ C. in a reaction-inert solvent. The 4"-methylene derivative thus produced is catalytically hydrogenated, either with or without protection of the 11- and 2'-hydroxy groups, to the corresponding 4"'-methyl derivative according to procedures described above.

Acid addition salts of the compounds of this invention wherein X or Z are a basic group are readily prepared by treating said compounds with an equimolar amount of the appropriate acid in a reaction-inert solvent for the compound. The acid addition salts are recovered by filtration if they are insoluble in the reaction-inert solvent, by precipitation, by addition of a non-solvent for said salt, or by evaporation of the solvent.

The novel oleandomycin derivatives described herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the LD$_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated four, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or non-aqueous such as fatty oils or vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

The following examples are provided solely for the purpose of illustration. Infrared (IR) spectra were measured as potassium bromide discs (KBr discs), and diagnostic absorption bands are reported in reciprocal centimeters (cm$^{-1}$). Nuclear magnetic resonance spectra (NMR) were measured in deuterochloroform (CDCl$_3$) and peak positions are expressed in parts per million (ppm) downfield from internal tetramethylsilane. The following abbreviations for peak shapes are used: s, singlet; d, doublet; t, triplet; q, quartet; and m, multiplet.

EXAMPLE 1

4"-Deoxy-4-Methyleneoleandomycin

Under a nitrogen atmosphere n-butyllithium (23.4 ml. of a 1.6 M hexane solution; 37.5 mmoles) was added dropwise to a $-70°$ C. solution of N,S-dimethylamino-S-phenylsulfoximine (6.3 g., 37.5 mmoles) in tetrahydrofuran (65 ml.) at such a rate that the temperature remained below −60° C. The reaction was stirred at −60° to −70° C. for one hour and a solution of the 11-trimethylsilyl (TMS) ether of 2′-acetyl-4″-deoxy-4″-oxooleandomycin (10.0 g., 12.5 mmoles) in tetrahydrofuran (35 ml.) then added dropwise at such a rate that the temperature remained below −60° C. The reaction was stirred for one hour at −60° to −70° C. after which 100 ml. of a 1:1 mixture of water:glacial acetic acid was added thereto followed by aluminum (15 g., 0.56 mole) as Al(Hg). The reaction was stirred for 2 hours with cooling in a water bath to maintain the temperature at 25° C. It was then filtered and the filtrate extracted with ethyl acetate (3×50 ml.). To the combined extract was added water (150 ml.) and the pH adjusted to 8.5 with 5% aqueous potassium carbonate. The ethyl acetate phase was separated, dried ($Na_2SO_4$) and evaporated under reduced pressure to a yellow oil (10 g.). The oil was chromatographed on silica gel (200 g.) using ethyl acetate as eluant. Fractions of 60 ml. each were collected. Fractions 40-160 were combined and concentrated to give a yellow oil. The oil was chromatographed on silica gel (200 g.) using ethyl acetate as eluant and fractions of 9 ml. each were collected. Fractions 60-160 were combined and evaporated to give 1.8 g. of the 11-trimethylsilyl ether of 2′-acetyl-4″-deoxy-4″-methyleneoleandomycin.

NMR: delta=5.40 (q, 1H); 5.00 (d, 2H); 3.35 (s, 3H); 2.25 (s, 6H).

The Al(Hg) was prepared by etching aluminum 15 g., 0.56 mole) with 0.1 N NaOH (50 ml.) until strong evolution of hydrogen occurred. The etched aluminum was then washed with water and treated with a 2% aqueous solution of $HgCl_2$ (50 ml.) with vigorous stirring. This treatment was repeated two more times after which the amalgam was washed successively with water (2×50 ml.), ethanol (2×50 ml.) and ether (2×50 ml.), and stored under ether until needed.

The 11-trimethylsilyl ether 2′-acetyl derivative was dissolved in ethyl acetate (25 ml.)-water (25 ml.) and the pH adjusted to 20 with 1 N HCl. The mixture was stirred for 45 minutes at room temperature and the pH then raised to 9.5 by addition of dilute aqueous NaOH. The ethyl acetate phase was separated and the aqueous phase extracted with ethyl acetate (2×50 ml.). The ethyl acetate extracts were combined, dried ($MgSO_4$) and evaporated under reduced pressure to a white foam. The foam was dissolved in methanol (100 ml.), the solution stirred at room temperature for 48 hours, then concentrated. The residue was chromatographed on silica gel (30 g.) first using chloroform (500 ml.) and then 3:1 ethyl acetate-acetone (500 ml.) as eluant. The eluate was monitored by thin layer chromatography (TLC) using the system 9 $CHCl_3$:1 $CH_3OH$. A vanillin spray (100 ml. of 85% $H_3PO_4$, 150 ml. of 2% $C_2H_5OH$ and 6 g. vanillin) and heat are used to develop the TLC.

Appropriate fractions are collected, combined and evaporated to yield 305 mg. of the title product as a white foam.

EXAMPLE 2

4″-Deoxy-4″-Methyloleandomycin

A solution of 4″-deoxy-4″-methyleneoleandomycin (210 mg., 3.07 mmoles) in absolute ethanol (20 ml.) was hydrogenated in a Paar shaker at 3.515 kg./cm.$^2$ (50 psi) in the presence of 100 mg. of 10% Pd/C for 18 hours at room temperature (20° C.). The catalyst was then removed from the reaction mixture by filtration and the filtrate removed under reduced pressure (aspirator) to afford the product as a white amorphous foam; 150 mg., 71% yield.

NMR: delta=5.40 (q, 1H); 3.23 (s, 3H); 2.25 (s, 6H).

EXAMPLE 3

4″-Deoxy-4″-Cyanomethyleneoleandomycin (syn- and anti-isomers)

To a solution of the 11-trimethylsilyl ether of 2′-acetyl-4″-deoxy-4″-oxooleandomycin (5.0 g., 6.2 mmoles) in ether (100 ml.) was added cyanomethyl diethyl phosphonate (1.09 g., 6.2 mmoles) and the mixture cooled to 0°-5° C. Sodium ethoxide (8.3 ml of a 0.74 M ethanol solution, 6.2 mmoles) was then added dropwise at 0°-5° C. and the resulting mixture stirred for one hour at 5° C. It was then added to water (100 ml.), the ether phase separated, dried ($Na_2SO_4$) and evaporated to an amorphous foam (5.2 g.). The foam was chromatographed on silica gel (200 g.) using ethyl acetate (1500 ml.) as first eluant, followed by 2:1 ethyl acetate:acetone (1200 ml.). Appropriate fractions were combined and evaporated to give 2.2 g. (43%) of the 11-trimethylsilyl ether of 2′-acetyl-4″-deoxy-4″-cyanomethyleneoleandomycin.

TLC (1:1 ethyl acetate:acetone): $R_f$=0.62.

IR=2225 cm$^{-1}$ (C≡N).

NMR: delta=5.40 (s, 1H); 3.38 (s, 3H); 2.23 (s, 3H); 0.66 (s, 9H).

It is arbitrarily assigned the syn-configuration.

Similarly, appropriate fractions afforded 0.6 g. (12%) of the more polar anti nitrile form (arbitrarily assigned).

TLC (1:1 ethyl acetate:acetone): $R_f$=0.45.

IR=22.5 cm$^{-1}$ (C≡N).

NMR: delta=5.38 (s, 1H); 3.26 (s, 3H); 2.23 (s, 6H); 2.03 (s, 3H); 0.116 (s, 9H).

The ether ester thus obtained (0.5 g.) was dissolved in tetrahydrofuran (10 ml.)-water (10 ml.), the pH adjusted to 2.0 with 1 N HCl, and the mixture stirred for 45 minutes at room temperature. Water (50 ml.)-ethyl acetate (50 ml.) was then added and the pH raised to 9.0 by addition of 1 N NaOH. The organic phase was separated, dried ($Na_2SO_4$) and evaporated to a foam (0.49 g.). The foam was dissolved in methanol (30 ml.), the solution stirred at room temperature for 2 days then evaporated under reduced pressure to give the title product as a foam (0.47 g.).

TLC (1:1 ethyl acetate:acetone): $R_f$=0.15.

IR: 2225 cm$^{-1}$ (C≡N).

NMR: delta=5.63 (q, 1H); 5.43 (s, 1H); 3.43 (s, 3H); 1.96 (s, 6H).

The compound was arbitrarily assigned the synconfiguration.

In like manner, the anti-isomer of the ether ester (0.5 g.) is converted to 4″-deoxy-4″-cyanomethyleneoleandomycin, anti isomer (0.45 g.).

TLC (1:1 ethyl acetate:acetone) $R_f$=0.12.

IR=2220 cm$^{-1}$ (C≡N)

NMR: delta=5.70 (q, 1H); 5.45 (s, 1H); 3.31 (s, 3H); 1.96 (s, 6H).

EXAMPLE 4

11-Trimethylsilyl Ether of 2′-Acetyl-4″-Deoxy-4″-Cyanomethyloleandomycin (C-4″-axial and equatorial forms)

A suspension of the 11-trimethylsilyl ether of 2′-acetyl-4″-deoxy-4″-cyanomethyleneoleandomycin (4.0 g., 4.8 mmoles), absolute ethanol (40 ml.) and 1.0 g. of 10%

Pd/C was hydrogenated at 3.515 kg./cm.$^2$ (50 psi) in a Paar shaker for 90 minutes. It was then filtered and the filtrate evaporated in vacuo to a white amorphous residue (3.8 g.) consisting of a mixture of the C-4''-axial and equatorial forms of 2'-acetyl-4''-deoxy-4-cyanomethyloleandomycin 11-trimethylsilyl ether. The mixture (1.6 g.) was separated by chromatography on 60 mesh silica gel (150 g.) using chloroform:isopropyl ether (98:2) as eluant. Fractions of 8 ml. volume were collected. Fractions 50–82 were combined and evaporated to give 420 mg. of product to which was assigned the C-4''-axial configuration ($R_f$=0.65 in 9:1 CHCl$_3$:CH$_3$OH). A more polar form (185 mg.) isolated from fractions 121–190 was assigned the C-4''-equatorial configuration ($R_f$=0.58 in 9:1 CHCl$_3$:CH$_3$OH). Fractions 81–120 afforded a mixture (210 mg.) of both forms.

EXAMPLE 5

4''-Deoxy-4''-Cyanomethyloleandomycin (mixture of axial and equatorial epimers at C-4'')

A solution of 2'-acetyl-4''-deoxy-4''-cyanomethyloleandomycin 11-trimethylsilyl ester, axial and equatorial forms, (0.42 g., 0.5 mmole) in tetrahydrofuran (10 ml.):water (10 ml.) was hydrolyzed according to the procedure given in Example 3 to give 0.37 g. of the title product.

TLC (1:1 ethyl acetate:acetone): $R_f$=0.1.
IR: 2240 cm$^{-1}$ (C≡N).
NMR: delta=5.65 (q, 1H); 3.40 (s, 3H); 2.33 (s, 6H).

EXAMPLE 6

4''-Deoxy-4''-(2-Aminoethyl)oleandomycin (C-4'' axial form)

To a solution of the 11-trimethylsilyl ether of 2'-acethyl-4''-deoxy-4''-cyanomethyloleandomycin, axial form at C-4'', (9.22 mg., 1.12 mmoles) in absolute ethanol (10 ml.) was added 3.6 ml. of a 1.88 M solution of ammonia in ethanol. Rhodium-on-alumina (368 mg. of 5% Rh/Al$_2$O$_3$) was added and the suspension hydrogenated at 3.16 kg./cm.$^2$ (45 psi) on a Paar shaker for 4–5 hours. The suspension was then filtered and the filtrate evaporated under reduced pressure. The residue was dissolved in ethyl acetate (50 ml.) and the solution washed first with 5% aqueous potassium carbonate solution (2×20 ml.), then with saturated sodium chloride solution (2×20 ml.) and dried (Na$_2$SO$_4$). Evaporation of the dried solution afforded 2'-acetyl-4''-deoxy-4''-(2-aminoethyl)oleandomycin, C-4 form (920 mg.), as a white amorphous foam.

The foam was dissolved in methanol (15 ml.) and the solution stirred at room temperature for 48 hours. It was then evaporated and the residue dissolved in 50% aqueous tetrahydrofuran (30 ml.). The pH of the solution was adjusted to 2.0 with 1 N HCl and the mixture stirred at room temperature for 2 hours. The pH was next adjusted to 9.5 with 1 N NaOH and the mixture added to ethyl acetate (100 ml.). The organic phase was separated, dried (Na$_2$SO$_4$) and evaporated to yield the title product (600 mg.) as a white amorphous foam.

TLC (50 CHCl$_3$:50 CH$_3$OH:3 NH$_4$OH): $R_f$=0.35.
NMR: delta=5.55 (q, 1H); 3.33 (s, 3H); 2.30 (s, 6H).

Similarly, the C-4'' equatorial form of 2'-acetyl-4''-deoxy-4''-cyanomethyloleandomycin 11-trimethylsilyl ester was converted to the C-4'' equatorial form of 4''-deoxy-4''-(2-aminomethyl)oleandomycin.

TLC (50 CHCl$_3$:50 CH$_3$OH:3 NH$_4$OH): $R_f$=0.25.
NMR: delta=5.63 (q, 1H); 3.40 (s, 3H); 2.36 (s, 6H).

EXAMPLE 7

11-Trimethylsilyl Ether of 2'-Acetyl-4''-Deoxy-4''-(2-Aminoethyl)oleandomycin (Mixture of C-4'' axial and equatorial epimers)

A mixture of 11-trimethylsilyl ether of 2'-acetyl-4''-deoxy-4''-cyanomethyloleandomycin axial and equatorial epimers (16.0 g., 19.4 mmoles), ammonium acetate (8.0 g.), 5% rhodium-on-alumina (8.0 g.) and absolute ethanol (275 ml.) was hydrogenated at 3.515 kg./cm.$^2$ (50 psi) overnight at room temperature in a Paar shaker. The reaction mixture was filtered, the catalyst washed with absolute ethanol, and the combined filtrate and wash poured into a mixture of potassium carbonate solution (1300 ml. of 5%) and ethyl acetate (400 ml.). After thorough mixing, the layers were separated and the organic layer extracted with saturated aqueous sodium chloride solution (3×100 ml.). The organic layer was dried (Na$_2$SO$_4$) and evaporated to give 17.2 g. of the title product contaminated with a small amount of sodium chloride and, by NMR assay, a small amount of the 2'-desacetyl product. It was used as in the procedure of the following example.

EXAMPLE 8

4''-Deoxy-4''-(2-Acetamidoethyl)oleandomycin (axial and equatorial epimers)

Acetic anhydride (2 ml.) was added to a solution of 2'-acetyl-4''-deoxy-4''-(2-aminoethyl)oleandomycin 11-trimethylsilyl ether (17.2 g., product of Example 7) and the mixture stirred for 3 hours at room temperature. Evaporation of the reaction mixture in vacuo gave 14.0 g. of the epimeric forms of the acetylated starting material.

The individual acetylated epimers were separated by chromatography on silica gel in acetone. Eighteen ml. fractions were collected. TLC monitoring using the system described in Example 1 and combination of appropriate fractions followed by evaporation thereof gave 2.6 g. of the axial form, less polar fraction; 1.5 g. of the equatorial form, more polar form, and a mixture (800 mg.) of epimers of 2'-acetyl-4''-deoxy-4''-(2-acetamidoethyl)oleandomycin 11-trimethylsilyl ether.

The axial epimer of 2'-acetyl-4''-deoxy-4''-(2-acetamidoethyl)oleandomycin 11-trimethylsilyl ether (2.6 g.) was stirred overnight at room temperature in methanol (25 ml.) to remove the 2'-acetyl group. The solution was then evaporated in vacuo and the residue taken up in tetrahydrofuran-water (100 ml. of 1:1) and the pH adjusted to 7.0 with 1 N HCl. The mixture was stirred for 2 hours at ambient temperature after which the pH was brought to 9.2 by addition of 5% K$_2$CO$_3$ solution. Extraction of the mixture with ethyl acetate (2×50 ml.) followed by washing of the combined extracts with water (25 ml.), saturated sodium chloride solution (25 ml.), drying (Na$_2$SO$_4$) and evaporation to dryness gave 2.29 g. of the axial epimer of the title compound.

NMR: delta=5.56 (q, 1H); 3.36 (s, 3H); 2.28 (s, 6H); 1.93 (s, 3H).

The equatorial epimer was similarly produced from the corresponding ether acetate:

NMR: delta=5.60 (q, 1H); 3.36 (s, 3H); 2.28 (s, 6H); 1.95 (s, 3H).

EXAMPLE 9

4"-Deoxy-4"-(2-Dibenzylaminomethyl)oleandomycin (axial and equatorial configurations at C-4")

Under a nitrogen atmosphere benzaldehyde (1.06 g., 10 mmoles) was added all at once with stirring to a solution of the C-4" axial and equatorial epimers of 11-trimethylsilyl ether of 2'-acetyl-4"-deoxy-4"-(2-aminoethyl)oleandomycin (2.07 g., 2.5 mmoles) and acetic acid (150 mg., 2.5 mmoles) in isopropanol (20 ml.) at −20° C. The mixture was stirred for 10 minutes and sodium cyanoborohydride (157 mg., 2.5 mmoles) then added. The reaction mixture was stirred and allowed to come to room temperature. It was then poured into water (200 ml.), layered with methylene chloride (200 ml.) and the pH adjusted to 9.5 with 1 N NaOH. The mixture was thoroughly mixed, the organic phase separated and evaporated to provide a tacky foam (1.8 g.). The foam, a mixture of the axial and equatorial epimers, of the 11-trimethylsilyl ether 2'-acetate of the desired product, was subjected to chromatography on silica gel (80 g.) using ethyl acetate as eluant. The eluate was monitored using the system of Example 1. Appropriate fractions were combined and evaporated to give three products. The less polar fraction (253 mg.) was arbitrarily assigned the axial configuration and the more polar form (124 mg.) the equatorial configuration. The product of intermediate polarity (500 mg.) was a mixture of the two epimers.

The reaction was repeated to provide additional quantities of the above products.

The axial form of the 11-trimethylsilyl ether 2'-acetate (434 mg.) was dissolved in methanol (10 ml.) and the solution stirred overnight at room temperature. Water (10 ml.) was added and the pH adjusted to 2.0 by addition of 0.5 N HCl. The mixture was stirred for 45 minutes at room temperature, ethyl acetate (25 ml.) added and the pH raised to 9.8 by addition of 5% $K_2CO_3$ solution. The organic phase was separated, washed with water (2×10 ml.), dried ($Na_2SO_4$) and evaporated to give 382 mg. of the axial epimer of the title compound as a foam.

TLC (1:1 ethyl acetate:acetone): $R_f=0.25$.

MS: m/e=352.

NMR: delta=7.36 (broad s, 10H); 5.66 (q, 1H); 3.66 (broad s, 4H); 3.23 (s, 3H); 2.33 (s, 6H).

In like manner, the equatorial epimer of the 11-trimethylsilyl ether 2'-acetate was converted to 535 mg. of the equatorial epimer of the title compound.

NMR: delta=7.30 (broad s, 10H); 5.55 (q, 1H); 3.56 (broad s, 4H); 3.16 (s, 3H); 2.26 (s, 6H).

In like manner, but using the appropriate ($R_4$-substituted)benzaldehyde in place of benzaldehyde, the epimeric forms of the following 4"-deoxy-4"-[2-di(substituted benzyl)aminoethyl]oleandomycin are produced. For convenience only the 2-di(substituted benzyl)amino ethyl group is indicated:

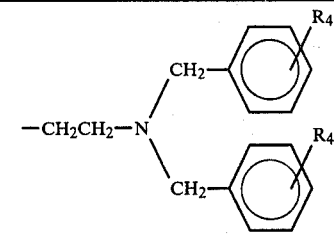

| $R_4$ | $R_4$ |
|---|---|
| 4-Cl | 2-$CH_3$ |
| 3-Br | 3-n-$C_3H_7$ |
| 2-Cl | 4-t-$C_4H_9$ |
| 4-$OCH_3$ | 4-$C_2H_5$ |
| 3-$OC_2H_5$ | 4-O—i-$C_3H_7$ |

EXAMPLE 10

4"-Deoxy-4"-(2-Benzylaminoethyl)oleandomycin (equatorial and axial epimers)

The procedure of Example 9 was followed but using an equimolar quantity of benzaldehyde in place of the excess benzaldehyde used in said example to give a mixture of the epimers of 2'-acetyl-4"-deoxy-4"-(2-benzylaminoethyl)oleandomycin 11-trimethylsilyl ether which was chromatographically separated (silica gel).

Deacetylation and hydrolysis of the 2'-acetyl and 11-trimethylsilyl groups of the individual epimers gave the title compounds:

Axial epimer:

MS: m/e=262.

NMR: delta=7.13 (s, 5H); 5.56 (q, 1H); 3.76 (s, 2H); 3.26 (s, 3H); 2.26 (s, 6H).

Equatorial epimer:

MS: m/e=262.

NMR: delta=7.26 (s, 5H); 5.56 (q, 1H); 3.80 (s, 2H); 3.31 (s, 3H); 2.28 (s, 6H).

The following 4"-deoxy-4"-[2-(substituted)benzylaminoethyl]oleandomycin are obtained as their axial and equatorial epimers by substituting the appropriate $R_4$-substituted benzaldehyde for benzaldehyde. Only the 2-(substituted)benzylaminoethyl group is listed for convenience.

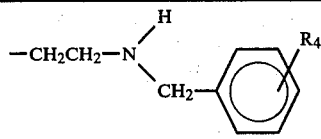

| $R_4$ | $R_4$ |
|---|---|
| 2-Cl | 2-$CH_3$ |
| 4-Cl | 4-$CH_3$ |
| 3-Br | 4-t-$C_4H_9$ |
| 2-$OCH_3$ | 3-$C_2H_5$ |
| 4-O—n-$C_4H_9$ | 3-$OC_2H_5$ |
| 4-O—i-$C_3H_7$ | |

EXAMPLE 11

4"-Deoxy-4"-(2-Phthalimidoethyl)oleandomycin (axial and equatorial isomers)

A mixture of N-carboethoxy phthalimide (889 mg., 4.06 mmoles), 2'-acetyl-4"-deoxy-4"-(2-aminoethyl- )oleandomycin 11-trimethylsilyl ether (3.2 g., 3.86 mmoles), triethylamine (410 mg., 4.06 mmoles) and N,N-dimethylformamide (15 ml.) was stirred at room temperature for two hours.

The reaction mixture was added to water (100 ml.) and the pH was adjusted to 9.5 (5% $K_2CO_3$). The water was extracted with ethyl acetate (3×100 ml.). The ethyl acetate fractions were combined and dried over $Na_2SO_4$. The ethyl acetate was evaporated under reduced pressure to yield 3.8 g. of the 2'-acetate 11-trimethylsilyl ether of the title compound as a tacky foam.

The foam was dissolved in ethyl acetate and chromatographed on silica gel (80 g.), 10 ml. fractions being collected. The fractions were monitored by TLC/acetone, using the detection system of Example 1. Appropriate fractions were combined and evaporated to give 198 mg. of the axial epimer from fractions 30–34 and 229 mg. of the equatorial epimer from fractions 61–74.

Deacylation and hydrolysis of the 2'-acetyl and 11-trimethylsilyl (TMS) group of the individual epimers according to the procedure of Example 9 afforded the axial and equatorial epimers of the title compound.

Axial epimer:
TLC: ($CHCl_3$:$CH_3OH$, 4:1) $R_f$=0.55.
NMR: delta=7.66 (m, 4H); 5.50 (q, 1H); 3.26 (s, 3H); 1.96 (s, 6H).

Equatorial epimer:
TLC: ($CHCl_3$:$CH_3OH$, 4:1) $R_f$=0.44.
NMR: delta=7.83 (m, 4H); 5.63 (q, 1H); 3.30 (s, 3H); 2.36 (s, 6H).

EXAMPLE 12

4"-Deoxy-4"-(2-Picolinoylamidoethyl)oleandomycin (epimeric mixture)

At room temperature N-hydroxysuccinimide (628 mg., 5.45 mmoles) was added to a suspension of picolinic acid (672 mg., 5.45 mmoles) in tetrahydrofuran. Dicyclohexylcarbodiimide (1.13 g., 5.45 mmoles) was then added and the mixture stirred to give, within 5–6 mintues, a heavy white precipitate. After stirring for an additional hour, the reaction was filtered and the filter cake washed with sufficient tetrahydrofuran to give a total filtrate of 50 ml.

To 40 ml. of the thus-prepared solution of activated ester was added 2'-acetyl-4"-deoxy-4"-(2-aminoethyl)oleandomycin trimethylsilyl ether (2.48 g., 3 mmoles) under a nitrogen atmosphere at room temperature. The reaction was stirred for 40 minutes and then diluted with water (100 ml.), and the pH adjusted to 9.5 by addition of 5% potassium carbonate. The reaction was then extracted with ethyl acetate (3×100 ml.). The ethyl acetate extracts were combined, dried over $Na_2SO_4$, and evaporated under reduced pressure to yield 2.1 g. of an amorphous foam. The foam was chromatographed on silica gel (80 g.)/acetone, 10 ml. fractions being collected, and the fractions monitored by TLC as described in Example 1. Fractions 39–57 were combined and evaporated to give 1.2 g. of an epimeric mixture of the 2'-acetyl-11-trimethylsilyl ethers of the title compound as a foam.

The thus-produced epimeric mixture (1.1 g.) was taken up in tetrahydrofuran (30 ml.)-water (15 ml.) and the pH adjusted to 2.5 with 2 N HCl. It was stirred at room temperature for 90 minutes then diluted with water (100 ml.) and the pH raised to 9.2 by addition of 5% potassium carbonate solution. Ethyl acetate extraction (3×100 ml.) of the basic mixture, followed by drying the combined extracts ($Na_2SO_4$) and evaporation gave a foam consisting essentially of an epimeric mixture of the 2'-acetyl derivatives of the title compound. Solvolysis according to the procedure of Example 1 and column chromatography (silica gel/chloroform) of the reaction mixture afforded an epimeric mixture of the title compound.

TLC: (9:1/$CHCl_3$:$CH_3OH$) $R_f$=0.80.
MS: m/e=277.
NMR: delta=8.66–7.33 (m, 5H); 5.60 (q, 1H); 3.40 (s, 3H); 2.31 (s, 6H).

EXAMPLE 13

4"-Deoxy-4"-[2-(3-Isoxazolylcarbonylamino)ethyl]oleandomycin

Following the procedure of Example 12, but using isoxazole-3-carboxylic acid (678 mg., 6 mmoles) in place of picolinic acid, and proportionate amounts of other reactants, the title compound was prepared as a mixture of its axial and equatorial epimers in 804 mg. yield.

TLC: ($CHCl_3$:$CH_3OH$, 9:1) $R_f$=0.4.
MS: m/e=267.
NMR: delta=8.30 (d, 1H); 6.60 (d, 1H); 5.41 (q, 1H); 3.26 (s, 3H); 2.13 (s, 6H).

EXAMPLE 14

4"-Deoxy-4"-[2-(4-tolyl sulfonamido)ethyl]oleandomycin

A Paar bottle was charged with 2'-acetyl-4"-deoxy-4"-cyanomethylene oleandomycin 11-trimethylsilyl ether (1.0 g., 1.2 mmoles) ammonium acetate (0.5 g., 6 mmoles), absolute ethanol (50 ml.) and 0.5 g. of 5% rhodium/alumina. Hydrogen, 3.515 kg./cm.$^2$ (50 psi) was introduced into the bottle and the mixture shaken and hydrogenated at room temperature for 18 hours. The reaction was then poured into a mixture of water (150 ml.) and ethyl acetate (350 ml.) and the pH adjusted to 2.5 with 1 N HCl. The mixture was thoroughly shaken, and the phases separated. The aqueous phase was layered with ethyl acetate (50 ml.), the pH raised to 6.0 by addition of 1 N NaOH and the mixture thoroughly shaken. This step was repeated but with pH adjustment to 9.5. The layers were separated and the basic aqueous phase extracted with ethyl acetate. The combined ethyl acetate extracts recovered by extraction at pH 9.5 were dried ($Na_2SO_4$) and the dry extract containing 2'-acetyl-4"-deoxy-4"-(2-aminoethyl)oleandomycin used directly in the next step.

To the extract produced above was added toluenesulfonyl chloride (0.23 g., 1.2 mmoles) and triethylamine (0.28 ml., 2.0 mmoles) and the mixture stirred at room temperature for 2 hours. It was then washed with water (2×50 ml.), dried ($Na_2SO_4$) and evaporated to a foam (900 mg.). The foam was chromatographed on silica gel using ethyl acetate as eluant. Appropriate fractions, determined by TLC, ethyl acetate/acetone (1:1), developed with vanillin spray (see Example 1), were combined and evaporated to give 0.52 g. of the title product as its 2'-acetyl derivative.

Solvolysis of the 2'-acetyl derivative in methanol (30 ml.) at room temperature for 3 days and evaporation of the solution gave 0.47 g. of the title product.

TLC: ($CHCl_3$:$CH_3OH$, 1:1) $R_f$=0.55.
NMR: delta=7.5 (AB quartet, J=9 Hz, 4H); 5.58 (q, 1H); 3.33 (s, 3H); 2.43 (s, 3H); 2.28 (s, 6H).

Repetition of the above procedure but using the appropriate $R_4$-substituted benzenesulfonyl chloride in place of toluenesulfonyl chloride affords the corresponding 4"-deoxy-4"-[2-(R₄-substituted benzenesulfonamido)ethyl]oleandomycin. For convenience only the 2-(R₄-substituted benzenesulfonamido)ethyl group is recorded.

$$-CH_2CH_2N\begin{matrix}H\\\\SO_2-\end{matrix}\!\!\!\!\!\!\!\bigcirc\!\!\!\!-R_4$$

| R₄ | R₄ |
|---|---|
| H | 4-t-C₄H₉ |
| 4-Cl | 2-t-C₄H₉ |
| 2-CH₃ | 3-sec-C₄H₉ |
| 3-CH₃ | 3-OCH₃ |
| 4-C₂H₅ | 4-OC₂H₅ |

EXAMPLE 15

2'-Acetyl-4"-Deoxy-4"-(Benzylideneaminomethylene)oleandomycin 11-Trimethylsilyl ether A mixture of diethylaminomethylphosphonate (1.35 g., 10 mmols) and benzaldehyde (1.02 ml., 10 mmole) was dissolved in dry toluene (25 ml.) and the toluene then evaporated at 40° C. under reduced pressure to azeotropically remove by-product water produced by Schiff base formation. This evaporation was repeated three times. The Schiff base was dissolved in dry tetrahydrofuran (20 ml.) in a flame dried round-bottom flask under a nitrogen atmosphere and the solution cooled to −70° C. Then, n-butyl lithium (4.3 ml. of a 2.2 molar solution in hexane; 9.5 mmols) was added, the temperature being held below −60° C. The resulting deep red solution was added dropwise over a period of one hour via cannula to a solution of 2'-acetyl 4"-deoxy-4-oxooleandomycin 11-trimethylsilyl ether (8.0 g., 10 mmols) in tetrahydrofuran (90 ml.) at −70° C. The reaction was then warmed to room temperature and added to a mixture of water (300 ml.)-ethyl acetate (300 ml.). The pH was adjusted to 9.0 by addition of 5% potassium carbonate solution and the organic phase separated, dried (Na₂SO₄) and evaporated to give the title product as a yellow amorphous product (5.2 g.). It is used in subsequent reactions as is.

Column chromatography of 0.5 g. of said product on 5 g. of silica gel using ethyl acetate as eluant afforded the pure product as a white amorphous foam.

NMR: delta=8.08 (s, 1H); 7.85–7.05 (m, 5H); 6.73 (s, 1H); 3.15 (s, 3H); 2.10 (s, 6H); 1.90 (s, 3H); 0.12 (s, 9H).

EXAMPLE 16

4"-Deoxy-4"-Benzylaminomethyloleandomycin

Sodium cyanoborohydride (100 mg., 1.58 mmoles) was added to a solution of 2'-acetyl-4"-deoxy-4"-(benzylideneaminomethylene)oleandomycin 11-trimethylsilyl ether (1.3 g., 1.44 mmols), methanol (20 ml.) and acetic acid (0.3 ml.) and the mixture stirred at room temperature for 2 hours. It was then poured into a mixture of ethyl acetate (50 ml.)-water (750 ml.) and stirred for 15 minutes. The aqueous phase was separated and extracted at pH 4.0, 5.5, 6.5 and 9.0 with ethyl acetate (50 ml.). The pH 5.5, 6.5 and 9.0 extracts were combined and evaporated under reduced pressure to give the 11-TMS ether of 2'-acetyl-4"-deoxy-4"-benzylaminomethyloleandomycin as a white foam (0.6 g.).

The foam was dissolved in methanol (30 ml.) and the solution stirred for 18 hours at room temperature. The reaction was then poured into a mixture of water (80 ml.)-ethyl acetate (80 ml.) and the pH adjusted to 2.5 with 1 N HCl. The phases were separated and the aqueous phase extracted at pH 4.0, 5.0, 6.5 and 9.5 with ethyl acetate (40 ml.). The pH 9.5 extract was dried (Na₂SO₄) and evaporated under reduced pressure to a white foam (0.55 g.).

NMR: delta=7.30 (s, 5H); 5.60 (q, 1H); 3.80 (broad s, 2H); 3.38 (s, 3H); 2.30 (s, 6H).

Following the procedure of Example 15 and the above Example, but replacing benzaldehyde with the appropriate R₄-substituted benzaldehyde, compounds of formula I wherein —CH₂Z is

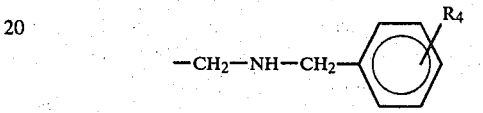

and each of R₁ and R₂ is hydrogen are produced. For convenience only the —CH₂Z group of the 4"-position is listed.

$$-CH_2-NH-CH_2-\!\!\!\bigcirc\!\!\!-R_4$$

| R₄ | R₄ |
|---|---|
| 2-Cl | 4-t-C₄H₉ |
| 4-Cl | 3-C₂H₅ |
| 3-Br | 4-OCH₃ |
| 2-CH₃ | 2-OC₂H₅ |
| 3-CH₃ | 4-O—n-C₄H₉ |
| 4-CH₃ | 3-O—i-C₃H₇ |

EXAMPLE 17

4"-Deoxy-4"-Aminomethyloleandomycin

A Paar shaker bottle was charged with 4"-deoxy-4"-benzylaminomethyloleandomycin (0.5 g.), ethanol (20 ml.), Pd/C (0.4 g. of 10%) and acetic (0.5 ml.) and the mixture hydrogenated at 3.515 kg./cm.² (50 psi) at room temperature for 20 hours. It was then filtered and the filtrate added to water (50 ml.)-ethyl acetate (50 ml.) and the pH adjusted to 2.5 with 1 N HCl. The aqueous phase was separated and extracted at pH 5.0 and 6.8 with ethyl acetate (25 ml. at each pH) and at pH 9.5 with ethyl acetate (2×25 ml.). The pH 9.5 extracts were combined, dried (Na₂SO₄) and evaporated under reduced pressure to a white foam (0.22 g.).

NMR: delta=5.60 (q, 1H); 3.41 (s, 3H); 2.33 (s, 6H); 3.26 [broad singlet which disappears on D₂O overlay, 2H (NH₂)].

EXAMPLE 18

4"-Deoxy-4"-[N-Benzyl-N-(4-tolylsulfonyl)aminomethyl]oleandomycin

A mixture of 2'-acetyl-4"-deoxy-4"-benzylaminomethyl oleandomycin (0.25 g., 0.3 mmole), methylene chloride (15 ml.), p-toluenesulfonyl chloride (67 mg., 0.35 mmole) and triethylamine (0.05 ml., 0.35 mmole) was stirred at room temperature for 18 hours. The reaction was then washed with saturated sodium chloride solution (3×10 ml.) and evaporated under reduced pressure. The residue was dissolved in ethyl acetate (15 ml.)-water (15 ml.) and aqueous ammonium hydroxide added slowly to remove excess p-toluenesulfonyl chloride. The organic phase was then separated, dried (Na₂SO₄) and evaporated under reduced pressure to give the 2'-acetyl derivative of the title product (0.22 g.) as a foam.

The 2'-acetyl derivative was then stirred for 18 hours in methanol (15 ml.) at room temperature. Evaporation of the reaction under reduced pressure gave 0.21 g. of the desired product.

NMR: delta=8.00–7.06 (m, 9H); 5.55 (q, 1H); 3.20 (s, 3H); 2.40 (s, 3H); 1.91 (s, 6H).

The 2'-acetyl-4"-deoxy-4"-benzylaminomethyloleandomycin reactant was prepared by adjusting the pH of a mixture of 2'-acetyl-4"-deoxy-4"-benzylaminomethyl oleandomycin 11-TMS ether to 2.5 with 1 N HCl and stirring the mixture for 45 minutes at room temperature. Water (50 ml.)-ethyl acetate (50 ml.) was then added and the pH raised to 9.0 by addition of 1 N NaOH. The organic phase was separated, dried (Na₂SO₄) and evaporated to give the desired reactant.

In like manner, but using the appropriate 2'-acetyl-4"-deoxy-4"-(R₄-substituted)benzylaminomethyl oleandomycin of Example 16 and the appropriate (R₄-substituted)benzenesulfonyl chloride affords corresponding compounds of formula I wherein the 4"-substitutent

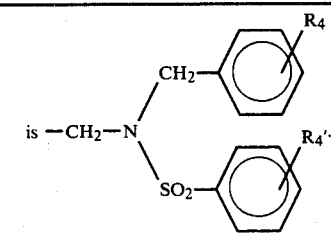

is —CH₂—N

| R₄ | R₄' | R₄ | R₄' |
|---|---|---|---|
| H | H | 2-Cl | H |
| H | 2-CH₃ | 4-Cl | H |
| 4-CH₃ | H | 3-Br | H |
| H | 4-Cl | 4-Cl | 4-CH₃ |
| H | 4-t-C₄H₉ | 3-OC₂H₅ | H |
| H | 3-sec-C₄H₉ | 3-OC₂H₅ | 2-Cl |
| H | 3-OCH₃ | 4-OCH₃ | 4-Cl |
| H | 4-OC₂H₅ | 4-t-C₄H₉ | H |
| 4-Cl | 4-C₂H₅ | 4-O—i-C₃H₇ | 3-CH₃ |

EXAMPLE 19

4"-Deoxy-4"-[(4-Toluenesulfonylamino)methyl]oleandomycin

4"-Deoxy-4"-[N-benzyl-N-(4-toluenesulfonylamino)-methyl]oleandomycin (0.15 g., 0.16 mmole) in ethanol (15 ml.) was hydrogenated over PtO₂ (0.1 g.) in a Paar shaker at 3.16 kg./cm.² (45 psi) for 18 hours at room temperature. The reaction was then filtered and evaporated under reduced pressure to a foam (0.14 g.).

Column chromatography on silica gel (8 g.) using tetrahydrofuran as eluant gave 0.054 g. of the title product as an amorphous solid. It was triturated in hexane to give 0.25 g. of product of better purity as determined by NMR.

NMR: delta=7.46 (dd, 4H); 5.26 (q, 1H); 3.26 (s, 3H); 2.36 (s, 3H); 1.91 (s, 6H).

Similarly, the remaining compounds of Example 18 are hydrogenolyzed to the corresponding (R₄-substituted)benzenesulfonyl derivatives.

EXAMPLE 20

3-Des(oleandrosyloxy)-3-(3",4"-Dehydro-4"-formyl-5"-methylpyran-1"-yloxy)oleandomycin A mixture of 2'-acetyl-4"-deoxy-4"-benzylideneaminomethylene oleandomycin 11-TMS ether (1.1 g., 1.1 mmoles), acetonitrile (15 ml.) and water (15 ml.) was adjusted to pH 2.5 by addition of 1 N HCl and the turbid solution stirred at room temperature for 45 minutes. Water (50 ml.) and ethyl acetate (50 ml.) were then added to the solution, the mixture thoroughly shaken and the phases separated. The aqueous phase was combined with ethyl acetate (50 ml.) and the pH adjusted to 9.0 with 1 N NaOH. The organic phase was separated, dried (Na₂SO₄) and evaporated under reduced pressure to a foam (0.71 g., 91%), the 2'-acetyl ester of the title product.

The 2'-acetyl derivative was dissolved in methanol (30 ml.), the solution stirred at room temperature for 18 hours and evaporated under reduced pressure to give the title compound (0.58 g.) as an amorphous solid.

MS: m/e = 125.0611 ± 0.8 ppm

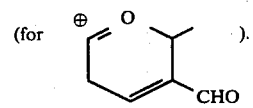

(for ).

NMR: delta=9.83 (s, 1H); 6.66 (t, 1H); 5.48 (t, 1H); 2.70 (s, 6H).

TLC (3:1 CHCl₃:CH₃OH): R_f=0.5.

EXAMPLE 21

3"-Desmethoxy-4"-Deoxy-4"-Formyloleandomycin

The unsaturated aldehyde product of Example 20, 3-des(oleandrosyloxy)-3-(3",4"-dehydro-4"-formyl-5"-methylpyran-1"-yloxy)oleandomycin (0.28 g., 0.4 mmole), ethanol (20 ml.) and Pd/C (0.03 g. of 10%) were placed in a Paar shaker and hydrogenated at 3.515 kg./cm.² (50 psi) for 90 minutes at room temperature. The reaction was then filtered and the filtrate evaporated under reduced pressure to give the title compound as a foam (0.25 g.).

NMR: delta=9.95 (d); 9.63 (d) integrating for 1H (mixture of diastereomers at C-4"); 5.50 (q, 1H); 2.23 (s, 6H).

EXAMPLE 22

3-Des(oleandrosyloxy)-3-(3",4"-Dehydro-4"-hydroxymethyl-5"-methylpyran-1"-yloxy)oleandomycin The 2'-acetyl derivative of 3-(desoleandrosyloxy)-3-(3",4"-dehydro-4"-formyl-5"-methylpyran-1"-yloxy)oleandomycin (1.1 g.) was dissolved in pyridine (3.5 ml.) and trimethylsilyl chloride (0.345 ml.) and hexamethyldisilizane (0.7 ml.) added. The mixture was stirred at room temperature for 24 hours and then poured into water (50 ml.). The pH was adjusted to 9.5 by addition of 5% aqueous NaHCO₃ solution and the extracted with ether (2×100 ml.). The ethereal extracts were combined, washed with saturated copper sulfate solution (2×50 ml.) and dried (Na₂SO₄). Evaporation gave 650 mg. of the 11-TMS derivative of 2'-acetyl-3-des(oleandrosyloxy)-3-(3'',4''-dehydro-4''-formyl-5''-methylpyran-1''-yloxy)oleandomycin as a white foam.

The thus-produced 2'-acetyl-11-TMS ether (0.2 g., 0.26 mmole) was dissolved in ethanol (5 ml.) and sodium borohydride (5 mg., 0.13 mmole) added. The mixture was stirred at room temperature for 30 minutes and then poured into water (50 ml.). Extraction of the aqueous mixture with ethyl acetate (2×20 ml.) followed by drying of the combined extracts (Na$_2$SO$_4$) and evaporation under reduced pressure gave the 2'-acetate 11-TMS ether of the title compound as a foam (0.184 g.).

Hydrolysis and methanolysis of the 11-TMS and 2'-acetyl groups of said compound according to the procedure of Example 3 gave 0.074 g. of the title compound as an amorphous solid.

MS: m/e=127.0760±0.1 ppm (for [structure]).

NMR: delta=5.55 (m, 2H); C-3'' and C-13 protons 2.30 (s, 6H).

EXAMPLE 23

4''-Deoxy-4''-Hydroxymethyloleandomycin

A solution of 2'-acetyl-4''-deoxy-4''-(benzylideneaminomethylene)oleandomycin 11-TMS ether (1.8 g., 2.0 mmoles) in ethanol (50 ml.) and water (25 ml.) was adjusted to pH 6.0 by addition of acetic acid. The mixture was stirred at room temperature for 2 hours, then adjusted to pH 8.5 with 1 N NaOH and poured into water (100 ml.). The solution was extracted with ethyl acetate (2×100 ml.) and the combined extracts washed with saturated sodium chloride solution dried and evaporated under reduced pressure to a yellow foam (1.38 g.).

The crude 2'-acetyl-4''-deoxy-4''-formyloleandomycin 11-TMS ether (1.3 g., 1.6 mmoles) thus produced was charged into a Paar shaker with ethanol (30 ml.), platinum dioxide (0.15 g.), zinc acetate (0.01 g.) and ferric chloride (0.01 g.) and hydrogenated at 3.515 kg./cm.$^2$ (50 psi) for 18 hours at room temperature. The reaction was filtered and evaporated under reduced pressure to a foam. The foam was dissolved in ethyl acetate (30 ml.) and water (30 ml.) and the pH raised to 8.5 by addition of 1 N NaOH. The ethyl acetate phase was separated, dried (Na$_2$SO$_4$) and evaporated to a foam. Column chromatography on silica gel using acetone as eluent gave 0.62 g. of the 2'-acetate-11-TMS ether of the title compound.

Methanolysis and hydrolysis of said 2'-acetate-11-TMS ether according to the procedure of Example 3 gave 0.3 g. of the title compound.

NMR: delta=5.58 (q, 1H); 3.41 (s, 3H); 2.33 (s, 6H).

EXAMPLE 24

3-Des(oleandrosyloxy)-3-(4''-hydroxymethyl-5''-methyltetrahydropyran-1''-yloxy)oleandomycin A solution of 3-des(oleandrosyloxy)-3-(3'',4''-dehydro-4''-hydroxymethyl-5''-methylpyran-1''-yloxy)oleandomycin (0.058 g., 0.09 mmole) in ethyl acetate (10 ml.) was hydrogenated in a Paar shaker over Pd/C (10 mg. of 10%) at 3.515 kg./cm.$^2$ (50 psi) for 18 hours at room temperature. The reaction was filtered and the filtrate evaporated under reduced pressure to an amorphous solid (0.45 g.).

NMR: delta=5.53 (q, 1H); 2.36 (s, 6H).

EXAMPLE 25

4''-Deoxy-4''-Methylsulfonylmethylene oleandomycin

A mixture of 2'-acetyl-4''-deoxy-4''-oxooleandomycin 11-TMS ether (2.0 g., 2.5 mmoles) and dimethyl methylsulfonylmethylphosphonate (0.6 g., 3.0 mmoles) in ethanol (20 ml.) was cooled to 15° C. Sodium ethoxide (4.6 ml. of 0.65 M; 3.0 mmoles) was then added dropwise over a 2 minute period, the temperature being held at 15° C. The mixture was then stirred for 3.5 hours at room temperature and then filtered to collect the solid product which formed (0.83 g.); the 2'-acetyl-11-TMS ether of the title compound.

Methanolysis and hydrolysis of said solid according to the procedure of Example 3 afforded the title compound as an amorphous solid.

TLC (1:1 ethyl acetate:acetone): R$_f$=0.15.

NMR: delta=6.03 (s, 1H); 5.51 (q, 1H); 3.15 (s, 3H); 2.90 (s, 3H); 2.16 (s, 6H).

EXAMPLE 26

4''-Deoxy-4''-Methylsulfonylmethyl oleandomycin

The procedure of Example 25 was repeated but on a 3-fold scale to give 2.9 g. of the 2'-acetyl-11-TMS derivative of 4''-deoxy-4''-methylsulfonylmethylene oleandomycin. Said compound was dissolved in ethyl acetate (50 ml.) and hydrogenated in a Paar shaker over Pd/C (1.5 g. of 10%) at 3.515 kg./cm.$^2$ (50 psi) at room temperature for 18 hours. Filtration of the reaction and evaporation of the filtrate gave 2.7 g. of the reduced compound, 2'-acetyl-4''-deoxy-4''-methylsulfonylmethyl oleandomycin 11-TMS ether.

Column chromatography on silica gel using ethyl acetate as eluent gave two products, the more polar being assigned the equatorial configuration at C-4'' and the less polar the axial form.

Removal of the 2'-acetyl and 11-TMS groups from said compounds by the methanolysis and hydrolysis procedures of Example 3 gave the equatorial and axial epimers of the title compound.

Axial Epimer:

TLC (acetone): R$_f$=0.18.

NMR: delta=5.63 (q, 1H); 3.38 (s, 3H); 2.96 (s, 3H); 2.30 (s, 6H).

Equatorial Epimer:

TLC (acetone): R$_f$=0.22.

NMR: delta=5.51 (q, 1H); 3.33 (s, 3H); 2.88 (s, 3H); 2.21 (s, 6H).

In like manner, but replacing dimethylsulfonylmethylphosphonate, with the appropriate dimethyl R$_3$'-sulfonylmethylphosphonate affords corresponding compounds wherein the 4''-substituent is =CH—S-(O)$_2$R$_3$' wherein R$_3$' is C$_2$H$_5$ or n-C$_4$H$_9$.

EXAMPLE 27

4''-Deoxy-4''-Phenylsulfonylmethylene oleandomycin

Sodium ethoxide (2.54 ml. of 1.97 M in C$_2$H$_5$OH; 5.0 mmoles) was added dropwise over a three minute period at 3° C. to a solution of 2'-acetyl-4''-deoxy-4''-oxooleandomycin 11-TMS ether (4.0 g., 5.0 mmoles) and diethyl phenylsulfonylmethylphosphonate (1.517 g., 5.19 mmoles) in ethanol (40 ml.). The mixture was stirred at 3° C. for 10 minutes then allowed to warm to 15° C. over a 20 minute period and then allowed to warm to room temperature. It was stirred for 75 minutes at said temperature and then poured into 5% potassium carbonate solution (150 ml.)-ethyl acetate (250 ml.) and thoroughly stirred. The organic phase was separated and the aqueous phase further extracted with ethyl acetate (150 ml.). The combined extracts were washed with brine, dried (MgSO4) and evaporated to an amorphous solid (4.15 g.).

Methanolysis and hydrolysis of the solid according to the procedure of Example 3 affords the title compound as an amorphous solid.

EXAMPLE 28

4"-Deoxy-4"-Phenylsulfonylmethyl oleandomycin

A solution of 2'-acetyl-4"-deoxy-4"-phenylsulfonylmethylene oleandomycin 11-TMS ether (4.15 g., 4.43 mmoles) in ethyl acetate (150 ml.) was hydrogenated in a Paar shaker at 3.515 kg./cm.$^2$ (50 psi) over Pd/C (6.3 g. of 10%) at room temperature for 18 hours. The reaction was then filtered, the filtrate added to water (100 ml.) and the pH adjusted to 2.5 with 6 N HCl. After stirring for two minutes, the pH was brought to pH 9.8 by addition of 5% K2CO3 and the mixture stirred. The ethyl acetate phase was separated, dried (MgSO4) and evaporated to a foam (3.5 g.).

Silica gel chromatography using ethyl acetate as eluant produced the axial and equatorial epimers of the 2'-acetyl-11-TMS ether.

Methanolysis and hydrolysis according to the procedure of Example 3 gave the axial and equatorial epimers of the title compound.

Axial epimer:
NMR: delta=8.06-7.33 (m, 5H); 3.10 (s, 3H); 2.33 (s, 6H).

Equatorial epimer:
NMR: delta=7.93-7.13 (m, 5H); 3.13 (s, 3H); 2.18 (s, 6H).

EXAMPLE 29

4"-Deoxy-4"-(4-tolylsulfonylmethyl)oleandomycin

The title compound was prepared according to the procedure of Examples 28 and 29, but substituting diethyl p-tolylsulfonylmethylphosphonate for the corresponding phenyl derivative.

NMR: delta=8.0-7.25 (d, d, 4H); 3.40 (s, 3H); 2.58 (s, 3H); 2.20 (s, 6H).

EXAMPLE 30

4"-Deoxy-4"-(2-Methoxyphenylsulfonylmethyl)oleandomycin

Following the procedures of Examples 28 and 29, the title compound was prepared by substituting diethyl (2-methoxyphenyl)sulfonylmethylphosphonate for the corresponding phenyl drivative.

NMR: delta=8.05-6.81 (m, 4H); 3.48 (s, 3H); 3.18 (s, 3H); 2.28 (s, 6H).

MS: m/e=313

(for 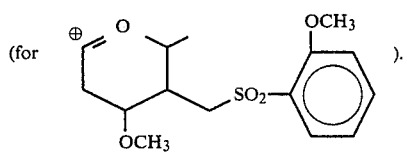 ).

Similarly, by substituting equimolar amounts of the appropriate diethyl (R4-substituted)phenylsulfonyloxymethylphosphonate for the corresponding phenyl derivative in the above procedure, formula I compounds wherein the 4"-substituent is

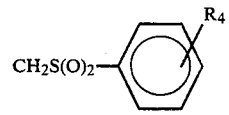

and each of $R_1$ and $R_2$ is hydrogen are prepared. For convenience only the $R_4$ variable is listed.

| $R_4$ | $R_4$ |
| --- | --- |
| 2-Cl | 3-OC3H7 |
| 4-Br | 4-t-C4H9 |
| 3-Cl | |

EXAMPLE 31

4"-Deoxy-4"-Methylthiomethyl oleandomycin

Repetition of the procedures of Examples 28 and 29 but substituting diethyl methylthiomethylphosphonate for diethylphenylsulfonylmethylphosphonate gave the title compound as an amorphous solid.

NMR: delta"5.61 (q, 1H); 3.39 (s, 3H); 2.31 (s, 6H); 2.16 (s, 3H).

The following compounds were similarly prepared using the appropriate diethylphosphonate derivative:

4"-deoxy-4"-methylsulfinylmethyl oleandomycin

NMR: delta=5.49 (q, 1H); 3.26 (s, 3H); 2.53 (s, 3H); 2.21 (s, 6H);

4"-deoxy-4"-phenylsulfinylmethyl oleandomycin

NMR: delta=5.56 (q, 1H); 3.29 (s, 3H); 2.19 (s, 6H).

EXAMPLE 32

The following compounds are prepared from appropriate diethylphosphonates of the formula

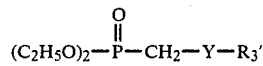

wherein Y is O, S, SO or SO2 and $R_3'$ is (C1-4)alkyl or

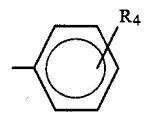

wherein $R_4$ is H, Cl, Br, (C1-4)alkyl or (C1-4)alkoxy by the procedures of Examples 28 and 29.

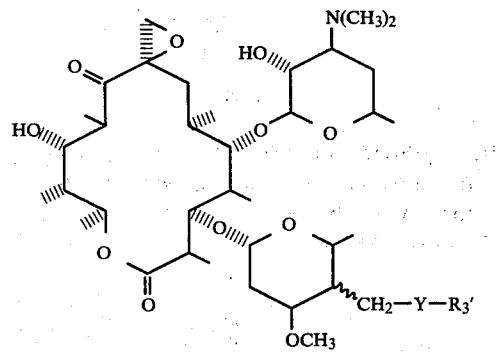

| Y | R3' | Y | R3' |
|---|---|---|---|
| O | H | O | 3-C2H5OC6H4 |
| O | CH3 | O | 3-(n-C4H9O)C6H4 |
| O | i-C3H7 | S | C2H5 |
| O | n-C4H9 | S | n-C4H9 |
| O | C6H5 | SO | C2H5 |
| O | 3-ClC6H4 | SO | n-C4H9 |
| O | 2-ClC6H4 | S | C6H5 |
| O | 4-CH3C6H4 | S | 2-ClC6H4 |
| O | 4-(t-C4H9)C6H4 | S | 4-BrC6H4 |
| O | 4-BrC6H4 | S | 3-(C3H7O)C6H4 |
| O | 2-CH3OC6H4 | S | 4-(t-C4H9)C6H4 |
| SO | 2-ClC6H4 | SO | 4-BrC6H4 |
| SO | 3-(C3H7O)C6H4 | SO | 4-(t-C4H9)C6H4 |

EXAMPLE 33

4''-Deoxy-4''-Carbethoxymethyl oleandomycin

To a solution of 2'-acetyl-4''-deoxy-4''-oxooleandomycin 11-TMS ether (2.0 g., 2.5 mmoles) and triethylphosphonoacetate (0.531 ml., 2.7 mmoles) in dry tetrahydrofuran (20 ml.) was added dropwise with stirring at −60° C., n-butyl lithium (1.13 ml. of 2.22 M in hexane) under a nitrogen atmosphere. The mixture was then allowed to warm to room temperature and stirred for 2.5 hours. It was then poured into a mixture of water (50 ml.) and ethyl acetate (50 ml.) and thoroughly mixed. The organic phase was separated, dried (Na2SO4) and evaporated to give 2.1 g. of 2'-acetyl-4''-deoxy-4''-carbethoxymethylene oleandomycin 11-TMS ether.

Silica gel chromatography using ethyl acetate as eluant gave 1.1 g. of the pure 2'-acetyl 11-TMS derivative.

Hydrogenation of said pure derivative according to the procedure of Example 26 and column chromatography of the product on silica gel using ether as eluant gave 0.7 g. of 2'-acetyl-4''-deoxy-4''-carbethoxymethyl oleandomycin. Further purification was achieved by silica gel chromatography using 1:1 ethyl acetate/chloroform as eluant.

Methanolysis and hydrolysis according to the procedure of Example 3 gave the title compound as a foam.

NMR: delta=5.46 (q, 1H); 3.23 (s, 3H); 2.20 (s, 6H).

In like manner, 4''-deoxy-4''-R3'OOC-CH2-oleandomycins wherein the 4''-substituent is as listed below are prepared by substituting equimolar amounts of the appropriate diethylphosphonoacetate for triethylphosphonoacetate. For convenience only the 4''-group is listed:

—CH2—COOCH3
—CH2—COO—n—C4H9
CH2—COO—i—C3H7
CH2—COOC6H5
CH2—COO—4—ClC6H4
CH2—COO—2—ClC6H4
CH2—COO—4—CH3C6H4
CH2—COO—4—(t—C4H9)C6H4
CH2—COO—2—CH3OC6H4
CH2—COO—4—(n—C4H9O)C6H4.

EXAMPLE 34

4''-Deoxy-4''-Carboxymethyl oleandomycin

Following the procedure of Example 34 but using diethylcarbobenzoxymethylphosphonate as the Wittig reagent, the title compound was prepared as an amorphous solid.

NMR: delta=3.33 (s, 3H); 2.91 (s, 6H indicating protonation of the dimethylamine group).

PREPARATION A

11-Trimethylsilyl Ether of 2'-Acetyl-4''-Dexoy-4''-Oxooleandomycin

To a suspension of 2'-acetyl -4''-deoxy-4''-oxooleandomycin (60.0 g., 0.083 mole) and imidazole (12.0 g., 0.176 mole) in N,N-dimethylformamide (36 ml.)-tetrahydrofuran (20 ml.) at −10° C. was added dropwise a solution of trimethylsilyl chloride (14 ml., 0.11 mole) in tetrahydrofuran (10 ml.) at such a rate that the temperature did not rise above −5° C. The mixture was stirred at −15° C. for one hour then poured into a mixture of ethyl acetate (300 ml.)-water (300 ml.) and the resulting mixture thoroughly mixed. The phases were then separated and the aqueous phase extracted with ethyl acetate (2×200 ml.) The ethyl acetate extracts were combined then washed with a saturated aqueous solution of sodium chloride. The extract was then dried (Na2SO4) and evaporated under reduced pressure (aspirator) to give 61.2 g. of the product as a foam.

NMR: delta=3.50 (s, 3H); 2.8 (s, 1H); 2.73 (s, 1H); 2.28 (s, 6H); 2.05 (s, 3H); 0.13 (s, 9H).

PREPARATION B

Diethylaminomethylphosphonate

A solution of benzylamine (60 ml., 0.55 mole) in water (200 ml.) was cooled to 5° C. and formaldehyde (1.45 mole of 37%; 1.8 moles) then added dropwise at such a rate as to keep the temperature below 25° C. A white gum separated. The mixture was stirred for one hour at room temperature after which the water was decanted and the gum washed with water (2×200 ml.). It was then taken up in ether (200 ml.), the ether solution washed with saturated sodium chloride solution (2×50 ml.) then dried (Na2SO4) and evaporated to give 1,3,5-tribenzyltrimethylenetriamine as an oil.

The oil was dissolved in toluene (200 ml.), the solution azetropically distilled until all water was removed, and then cooled to room temperature. Diethyl phosphite (71 ml., 0.55 mole) was then added dropwise and the resulting mixture heated to reflux for four hours. It was filtered and evaporated under reduced pressure to give an oil. The oil was dissolved in ether (300 ml.), the solution cooled to 5° C. and an excess of hydrogen chloride gas passed into the solution. The gum which separated crystallized on stirring. It was filtered and washed with ether. The hygroscopic solid was immediately dissolved in chloroform (200 ml.) and the solution evaporated in vacuo to a yellowish oil which crystallized on storage in vacuo. Yield=80 g. of diethyl benzylaminomethylphosphonate hydrochloride.

The thus-produced compound was debenzylated as follows. A mixture of said compound (1.7 g.), ethanol (20 ml.), and Pd/C (1.0 g. of 10%) was hydrogenated in a Paar shaker at 3.16 kg./cm.² (45 psi) for 18 hours at room temperature. The mixture was filtered and evaporated under reduced pressure to give a crystalline solid. The solid was dissolved in chloroform (10 ml.), triethylamine (1 ml.) added and the solution stirred for 10 minutes. Ether (100 ml.) was added to precipitate triethylamine hydrochloride which was removed by filtration. Evaporation of the filtrate gave 0.85 g. of diethyl aminomethylphosphonate as a yellowish oil.

PREPARATION C

Diethyl Carbobenzoxymethyl Phosphonate

Ethyl phosphonate (5.6 g.) was dissolved in 1 N NaOH (25 ml.) and stirred at room temperature for 18 hours. Acidification of the mixture to pH 3 with 1 N HCl and extraction of the acid solution with ethyl acetate gave, after evaporation of the ethyl acetate, diethyl carboxymethyl phosphonate (5.0 g.) as an oil which was used directly in the next step.

Diethyl carboxymethylphosphonate (981 mg., 5 mmoles) was dissolved in methylene chloride (20 ml.) and solution cooled to 0° C. Oxalyl chloride (634 mg., 5 mmoles) was added and the mixture stirred for one hour at 0° C. Benzyl alcohol (5 mmoles) and triethylamine (6.5 mmoles) were added, and the resulting mixture stirred at room temperature for 18 hours. It was then poured into water (100 ml.) and the title product extracted with ethyl acetate (2×30 ml.). Evaporation afforded the product as a colorless oil.

I claim:
1. A compound having the formula

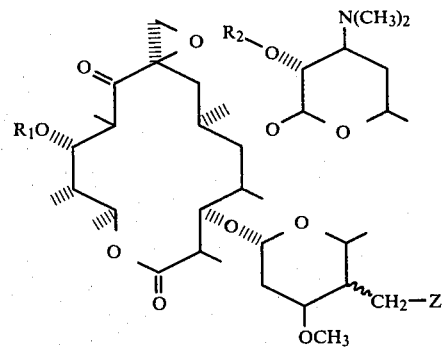

wherein
$R_1$ is hydrogen or trimethylsilyl;
$R_2$ is hydrogen or alkanoyl having from two to three carbon atoms;
Z is H, $OR_3$, $COOR_3$, $SR_3'$, $S(O)R_3'$, $S(O)_2R_3'$, CN or —$(CH_2)_n$—$NR_5R_6$;
$R_3$ is hydrogen, alkyl having from one to four carbon atoms or

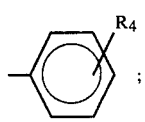

$R_3'$ is alkyl having from one to four carbon atoms or

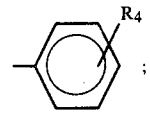

$R_4$ is hydrogen, chloro, bromo, alkyl having from one to four carbon atoms or alkoxy having from one to four carbon atoms;
$R_5$ is hydrogen or

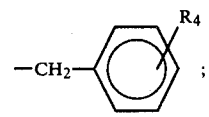

$R_6$ is hydrogen,

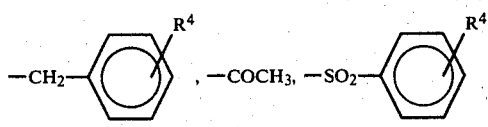

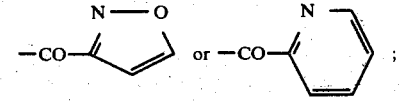

$R_5$ and $R_6$ when taken together with the nitrogen to which they are attached are phthalimido; and
n is 0 or 1;
or a pharmaceutically acceptable acid addition salt thereof.

2. A compound according to claim 1 wherein Z is —$(CH_2)_n$—$NR_5R_6$.

3. A compound according to claim 2 wherein each of $R_1$ and $R_2$ is hydrogen.

4. A compound according to claim 3 wherein $R_5$ is hydrogen and n is 0.

5. A compound according to claim 4 wherein $R_6$ is

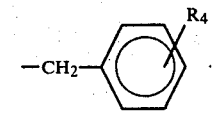

6. The compound according to claim 5 wherein $R_4$ is hydrogen.

7. The compound according to claim 3 wherein n is 0, and each of $R_5$ and $R_6$ is hydrogen.

8. The compound according to claim 3 wherein $R_5$ and $R_6$ together with the nitrogen to which they are attached represent phthalimido and n is 1.

9. A compound according to claim 1 wherein Z is $SO_2R_3'$.

10. The compound according to claim 9 wherein $R_3'$ is methyl, each of $R_1$ and $R_2$ is hydrogen.

11. A compound according to claim 1 wherein Z is —CN.

12. A compound having the formula

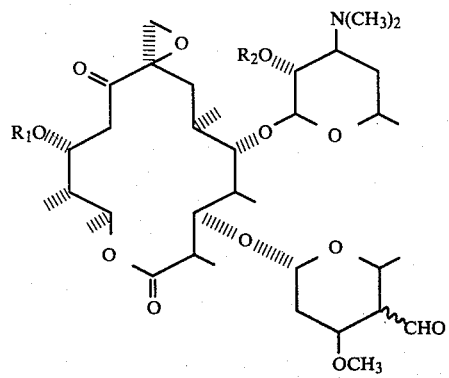

wherein
R₁ is hydrogen or trimethylsilyl; and
R₂ is hydrogen or alkanoyl having from two to three carbon atoms; or a pharmaceutically acceptable acid addition salt thereof.

13. The compound according to claim 12 wherein each of $R_1$ and $R_2$ is hydrogen.

14. A compound having the formula

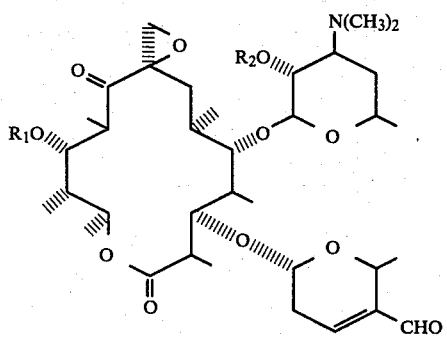

wherein
R₁ is hydrogen or trimethylsilyl; and
R₂ is hydrogen or alkanoyl having from two to three carbon atoms.

15. The compound according to claim 14 wherein each of $R_1$ and $R_2$ is hydrogen.

16. A compound having the formula

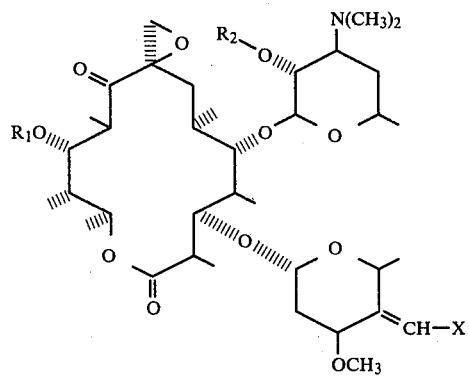

wherein
R₁ is hydrogen or trimethylsilyl;
R₂ is hydrogen or alkanoyl having from two to three carbon atoms;
X is H, CN,

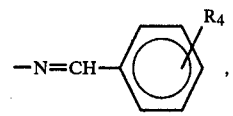

COOR₃, SR₃', S(O)R₃' or S(O)₂R₃',
R₃ is hydrogen, alkyl having from one to four carbon atoms or

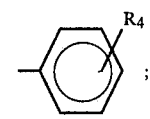

R₃' is alkyl having from one to four carbon atoms or

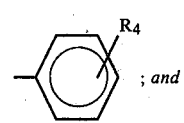

; and

R₄ is hydrogen, chloro, bromo, alkyl having from one to four carbon atoms or alkoxy having from one to four carbon atoms.

17. A compound according to claim 16 wherein X is H.

18. A compound according to claim 16 wherein X is CN.

19. The compound according to claim 18 wherein $R_1$ is trimethylsilyl and $R_2$ is acetyl.

* * * * *

UNITED STATES PATENT AND TRADEMARK OFFICE
CERTIFICATE OF CORRECTION

PATENT NO. : 4,336,368
DATED : June 22, 1982
INVENTOR(S) : Arthur A. Nagel

It is certified that error appears in the above-identified patent and that said Letters Patent are hereby corrected as shown below:

Title Page, Item [54], "4-Deoxy-4-" should read -- 4"-Deoxy-4"- --.

ABSTRACT, formula (b) should read,

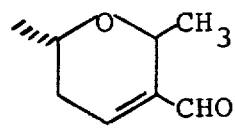

Col. 1, line 60, "4-" should read -- 4"- --.
Col. 8, line 64, "4-" should read -- 4"- --.
Col. 11, line 5, "4-" should read -- 4"- --.
Col. 12, line 25, after "as", insert -- is --.
Col. 17, line 39, "4-" should read -- 4"- --.

Signed and Sealed this

Eleventh Day of January 1983

[SEAL]

Attest:

GERALD J. MOSSINGHOFF

Attesting Officer

Commissioner of Patents and Trademarks